(12) United States Patent
Hashimoto

(10) Patent No.: US 12,310,863 B2
(45) Date of Patent: May 27, 2025

(54) KNEE JOINT, POSTURE CALCULATOR, METHOD OF CONTROLLING KNEE JOINT, AND NON-TRANSITORY COMPUTER-READABLE MEDIUM RECORDING PROGRAM FOR CONTROLLING KNEE JOINT

(71) Applicant: NABTESCO CORPORATION, Tokyo (JP)

(72) Inventor: Hiroaki Hashimoto, Tokyo (JP)

(73) Assignee: NABTESCO CORPORATION, Tokyo (JP)

(*) Notice: Subject to any disclaimer, the term of this patent is extended or adjusted under 35 U.S.C. 154(b) by 617 days.

(21) Appl. No.: 17/560,462

(22) Filed: Dec. 23, 2021

(65) Prior Publication Data

US 2022/0202597 A1 Jun. 30, 2022

(30) Foreign Application Priority Data

Dec. 25, 2020 (JP) ................................ 2020-217642

(51) Int. Cl.
| | |
|---|---|
| A61F 2/64 | (2006.01) |
| A61F 2/68 | (2006.01) |
| A61F 2/70 | (2006.01) |
| A61F 5/01 | (2006.01) |
| B25J 9/00 | (2006.01) |
| B62D 57/032 | (2006.01) |
| A61F 2/76 | (2006.01) |
| B25J 9/16 | (2006.01) |

(Continued)

(52) U.S. Cl.
CPC ............... *A61F 2/644* (2013.01); *A61F 2/64* (2013.01); *A61F 2/68* (2013.01); *A61F 5/0125* (2013.01); *B25J 9/0006* (2013.01); *B62D 57/032* (2013.01); *A61F 2002/704* (2013.01); *A61F 2002/7625* (2013.01); *A61F 2005/0155* (2013.01); *B25J 9/16* (2013.01); *G05B 13/00* (2013.01); *G05B 15/00* (2013.01); *G05B 15/02* (2013.01); *G05D 1/00* (2013.01)

(58) Field of Classification Search
None
See application file for complete search history.

(56) References Cited

U.S. PATENT DOCUMENTS

2019/0167988 A1 6/2019 Shahriari et al.

FOREIGN PATENT DOCUMENTS

| | | |
|---|---|---|
| JP | 2011220825 A | 11/2011 |
| JP | 2012501739 A | 1/2012 |

(Continued)

OTHER PUBLICATIONS

EPO Extended European Search Report for corresponding EP Application No. 21217530.1; Issued May 13, 2022.

(Continued)

*Primary Examiner* — David H Willse
(74) *Attorney, Agent, or Firm* — CANTOR COLBURN LLP

(57) ABSTRACT

A posture calculator that calculates the posture of a moving object based on a first hypercomplex number derived based on a detection result from an angular velocity sensor for detecting an angular velocity of the moving object and a second hypercomplex number that is derived based on a detection result from an angle sensor for detecting an angle of the moving object and that has the same number of terms as that of the first hypercomplex number.

12 Claims, 6 Drawing Sheets

(51) Int. Cl.
    *G05B 13/00*     (2006.01)
    *G05B 15/00*     (2006.01)
    *G05B 15/02*     (2006.01)
    *G05D 1/00*     (2006.01)

(56) References Cited

FOREIGN PATENT DOCUMENTS

| | | |
|---|---|---|
| JP | 2013054009 A | 3/2013 |
| JP | 2015217053 A | 12/2015 |
| JP | 2020110332 A | 7/2020 |
| WO | 2010027968 A2 | 3/2010 |
| WO | 2011026086 A1 | 3/2011 |

OTHER PUBLICATIONS

JPO Notification of Reason(s) for Refusal for corresponding JP Application No. 2020-217642; Issued Jun. 18, 2024.

KNEE JOINT, POSTURE CALCULATOR, METHOD OF CONTROLLING KNEE JOINT, AND NON-TRANSITORY COMPUTER-READABLE MEDIUM RECORDING PROGRAM FOR CONTROLLING KNEE JOINT

CROSS REFERENCE TO RELATED APPLICATIONS

The present invention claims priority under 35 U.S.C. § 119 to Japanese Application No. 2020-217642 filed Dec. 25, 2020, the entire content of which is incorporated herein by reference.

BACKGROUND OF THE INVENTION

1. Field of the Invention

The present invention relates to a knee joint, a posture calculator, a method of controlling a knee joint, and a computer-readable medium recording a program for controlling a knee joint.

2. Description of the Related Art

Conventionally, various types of development have been made on prosthetic legs that assist the wearer's walking. As a result of technological development of prosthetic legs, the prosthetic legs have been developed not only to support the weight of the wearer but also to have a desired posture according to the movement such as walking of the wearer. In calculating the posture of a prosthetic leg, a technology has been proposed in which an angular velocity sensor is used to perform control in consideration of rotation and posture (posture control using a quaternion) (for example, Patent Literature 1).

[Patent Literature 1] Japanese Patent Application Publication NO. 2020-110332

By controlling the posture of a prosthetic leg using a quaternion, it has become possible to calculate not only the rotation of the prosthetic leg but also the posture, and a technology has been developed that allows for control according to the walking motion of the wearer. However, the detection result of an angular velocity sensor is not always correct, and if an error occurs in the detection result, highly accurate posture control cannot be performed. It is conceivable to use a filter applied in advance in order to correct the error in the detection result of the angular velocity sensor. However, a filter is set for each scene on the assumption of various motion scenes, and its versatility is insufficient.

SUMMARY OF THE INVENTION

A purpose of the present invention is to provide a knee joint that enables the posture of the knee joint to be corrected according to various situations when controlling the posture of the knee joint using a detection result from an angular velocity sensor.

A posture calculator for achieving the above purpose calculates the posture of a moving object based on a first hypercomplex number derived based on a detection result from an angular velocity sensor for detecting an angular velocity of the moving object and a second hypercomplex number that is derived based on a detection result from an angle sensor for detecting an angle of the moving object and that has the same number of terms as that of the first hypercomplex number.

DETAILED DESCRIPTION OF THE INVENTION

The embodiment of the present invention is now described in the following. The present invention can be applied to various apparatuses that perform posture control independently on their own by using a detection result from an angular velocity sensor provided in the apparatuses without receiving mechanical support from the outside. Such apparatuses include moving objects such as drones and autonomous travelling automated carts, in addition to electronically controlled knee joints for prosthetic legs explained in the following embodiments.

In the following explanation, two types of three-dimensional Cartesian coordinate systems, a fixed system and a rotating system, may be used as terms indicating directions. In a coordinate system at rest, three axes are determined based on a state in which the wearer of a prosthetic leg stands upright. The X-axis extends in the width direction of the wearer, the Y-axis extends in the front-back direction of the wearer, and the Z-axis extends in the height direction of the wearer.

Figure 1:
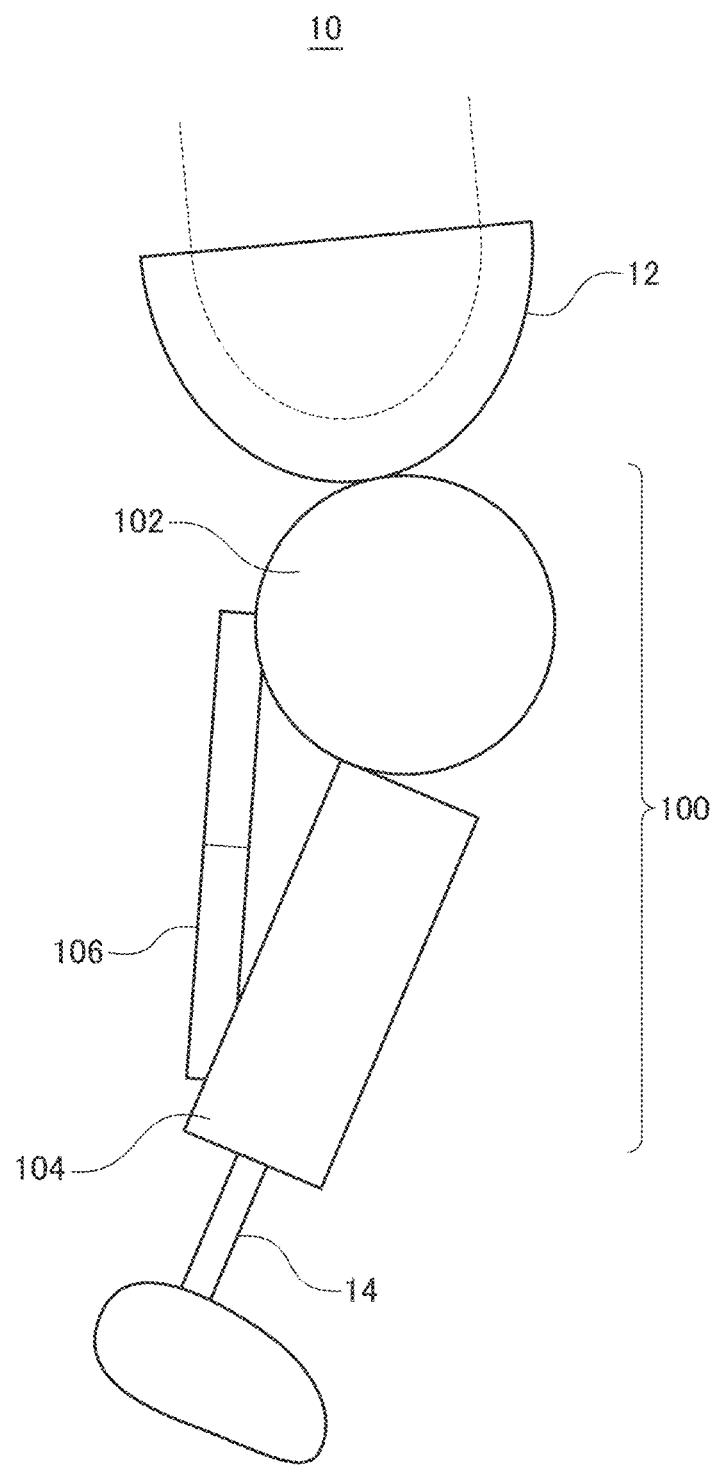
FIG. 1 is a schematic view of an above-knee prosthesis including an electronically controlled knee joint according to an embodiment.

FIG. 1 is a schematic view of an above-knee prosthesis including an electronically controlled knee joint (hereinafter, simply referred to as "knee joint") according to an embodiment. An above-knee prosthesis 10 includes a socket 12, a knee joint 100, and a foot-ankle assembly 14. The socket 12 encloses the wearer's stump. The foot-ankle assembly 14 functions as a wearer's foot. The knee joint 100 is connected between the socket 12 and the foot-ankle assembly 14. The knee joint 100 serves as a knee joint that controls the angle of the foot-ankle assembly 14 with respect to the socket 12 according to a state such as the posture of the knee joint 100.

The knee joint 100 includes a thigh connection part 102, a shank part 104, and a drive auxiliary part 106. The thigh connection part 102 is non-rotatably connected to the socket 12. The shank part 104 is connected to the thigh connection part 102 rotatably around the X axis. The shank part 104 is non-rotatably connected to the foot-ankle assembly 14. The drive auxiliary part 106 is connected between the thigh connection part 102 and the shank part 104. The drive auxiliary part 106 is constituted with an expandable drive mechanism such as a pneumatic or hydraulic cylinder. One end of the drive auxiliary part 106 is connected to the thigh connection part 102, and the other end is connected to the shank part 104. The driving or stopping of the drive auxiliary part 106 is controlled by a control unit described later. When the drive auxiliary part 106 is extended, the angle between the thigh connection part 102 and the shank part 104 around the X axis increases and approaches 180 degrees, and the thigh connection part 102 and the shank part 104 are aligned in a straight line. When the drive auxiliary part 106 contracts, the angle between the thigh connection part 102 and the shank part 104 around the X axis decreases, and the thigh connection part 102 and the shank part 104 form a predetermined angle (for example, 90 degrees) so as to be able to respond to the seating movement or the like of the wearer. When the expansion and contraction of the drive auxiliary part 106 is restricted, the angle between the thigh connection part 102 and the shank part 104 is fixed to the current angle. The knee joint 100 controls the angle between the thigh connection part 102 and the shank part 104 by expanding, contracting, or limiting the expansion and contraction of the drive auxiliary part 106 and even controls the angle of the foot-ankle assembly 14 with respect to the socket 12.

Figure 2:
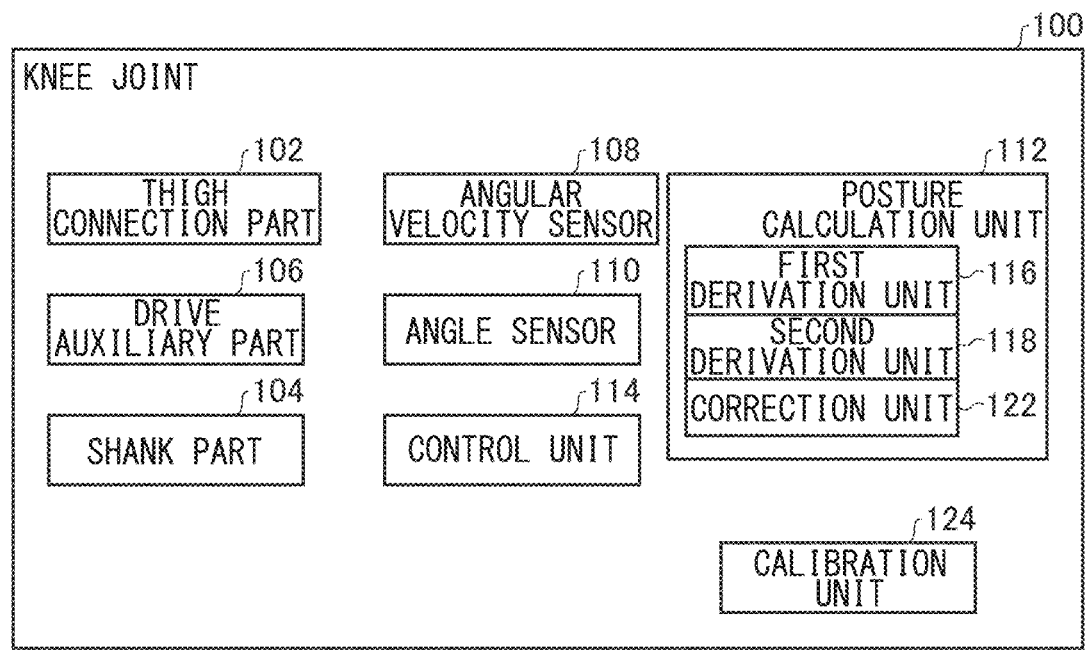
FIG. 2 is a block diagram showing a schematic configuration of a knee joint.

FIG. 2 is a block diagram showing a schematic configuration of a knee joint. Each block shown in FIG. 2 is implemented in hardware such as elements, electronic circuits, or mechanical devices such as a processor, a CPU, and a memory of a computer, and in software such as a computer program. The figure depicts functional blocks implemented by the cooperation of the hardware and the software. Thus, a person skilled in the art should appreciate that there are many ways of accomplishing these functional blocks in various forms in accordance with the components of hardware, software, or the combination of both. The hardware may be housed in either the thigh connection part 102 or the shank part 104, or may be attached to the knee joint 100 as an independently provided control device.

As shown in FIG. 2, the knee joint 100 includes an angular velocity sensor 108, an angle sensor 110, a posture calculation unit 112, and a control unit 114 in addition to the thigh connection part 102, the drive auxiliary part 106, and the shank part 104.

The angular velocity sensor 108 detects the angular velocity of the shank part 104. A gyro sensor can be used as the angular velocity sensor 108. The angular velocity sensor 108 is housed in the shank part 104. The angular velocity sensor 108 detects the angular velocity of the shank part 104 around the X-axis, the Y-axis, and the Z-axis around a connecting part with the thigh connection part 102 and supplies the detection result to the posture calculation unit 112.

The angle sensor 110 detects the angle of the shank part 104 with respect to the coordinate system at rest (vertical or azimuth direction). An acceleration sensor or a geomagnetic sensor can be used as the angle sensor 110. The detection result of the angle sensor 110 is supplied to the posture calculation unit 112. A 6-axis inertial sensor in which the angle sensor 110 and the angular velocity sensor 108 are combined may be used.

The posture calculation unit 112 calculates the posture of the shank part 104 based on the detection results of the angular velocity sensor 108 and the angle sensor 110.

The posture calculation unit 112 includes a first derivation unit 116, a second derivation unit 118, and a correction unit 122. The posture calculation unit 112 calculates the posture of the shank part 104 based on a hypercomplex number in three dimensions derived from the first derivation unit 116 and a hypercomplex number in three dimensions derived by the second derivation unit 118. The method of obtaining the posture of the shank part 104 will be described later.

The first derivation unit 116 derives the first hypercomplex number based on the detection result from the angular velocity sensor 108. The first hypercomplex number is obtained by deriving a quaternion that indicates how much a rotating coordinate system that rotates with the knee joint 100 has rotated with respect to a coordinate system at rest and then converting the quaternion into a hypercomplex number in three dimensions. The derived ternary number is supplied to the correction unit 122. The quaternion is expressed as a unit vector or an expression with four terms related to the angle of rotation. The following Expression 1 is a quaternion representing a general rotation. The derivation of a quaternion is an expression used to explain the logic of calculation, and it is not always necessary to derive a quaternion and hold the quaternion as information or write the quaternion out in a series of calculation processes explained below.

$$q = \cos\frac{\theta}{2} + n\sin\frac{\theta}{2} = q_0 + q_1 i + q_2 j + q_3 k \qquad \text{Expression 1}$$

where n represents a unit vector having a magnitude of 1, $q_0^2+q_1^2+q_2^2+q_3^2=1$ is established, and $\theta$ represents the angle of rotation.

The second derivation unit 118 derives a second hypercomplex number based on the detection result of the angle sensor 110. The second hypercomplex number indicates how much the rotating coordinate system that rotates with the knee joint 100 has rotated with respect to the coordinate system at rest. The second hypercomplex number is a hypercomplex number in three dimensions with less terms than a quaternion.

When correction is required, the correction unit 122 corrects the posture of the shank part 104 calculated from the detection results of the angular velocity sensor 108 and the angle sensor 110. The correction unit 122 makes the correction using a filter such as a Kalman filter or a complementary filter. The correction unit 122 makes the correction according to a predetermined condition such as every time the posture of the shank part 104 is calculated, for every predetermined time cycle, or after the posture of the shank part 104 is calculated for a predetermined number of times.

The posture calculation unit 112 supplies information regarding the posture of the shank part 104 not corrected by the correction unit 122 and information regarding the posture of the shank part 104 corrected by the correction unit 122 to the control unit 114 as posture information.

The control unit 114 controls the drive auxiliary part 106 based on the posture information supplied from the posture calculation unit 112. The posture information of the shank part 104 used by the control unit 114 is a value calculated by the posture calculation unit 112 or calculated and corrected by the posture calculation unit 112. For example, when the landing movement of the wearer is estimated from the posture of the shank part 104 indicated by the posture information, the control unit 114 extends the drive auxiliary part 106 to prepare for the landing, and further restricts the driving such that the shank part 104 does not rotate around the X-axis with respect to the thigh connection part 102 when the center of gravity of the wearer is on the prosthesis side.

The knee joint 100 further includes a calibration unit 124. The calibration unit 124 estimates the drift of the angular velocity sensor 108 using the hypercomplex number in three dimensions obtained by the first derivation unit 116 and calibrates the angular velocity sensor 108 so as to cancel the drift.

Figure 3:
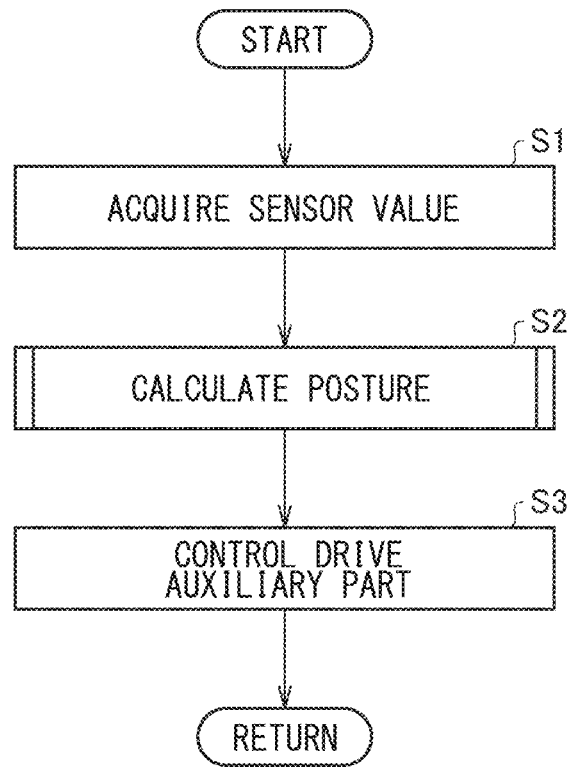
FIG. 3 is a flow chart showing a series of movements of the knee joint.

Next, the operation of the knee joint 100 will be described. FIG. 3 is a flow chart showing a series of movements of the knee joint. When the power of the knee joint 100 is turned on and the series of movements are started, the knee joint 100 acquires a sensor value in step S1. This process is executed when the posture calculation unit 112 acquires the detection results from the angular velocity sensor 108 and the angle sensor 110. Next, in step S2, the knee joint 100 calculates the posture of the shank part 104. This process will be described later. Next, in step S3, the knee joint 100 controls the drive auxiliary part 106. This process is executed by the control unit 114 controlling the drive auxiliary part 106 based on the posture information obtained in step S2.

Figure 4:
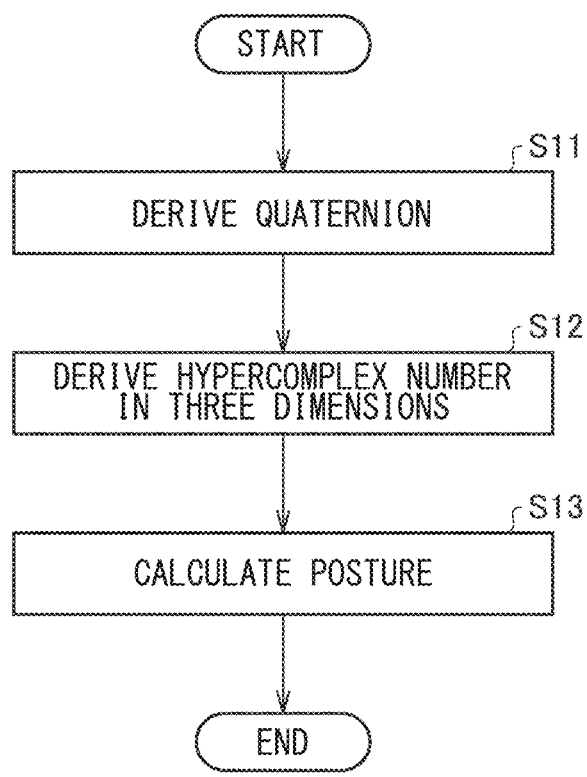
FIG. 4 is a flow chart specifically showing the process in step S2 of FIG. 3.

FIG. 4 is a flow chart showing a series of processes of the posture calculation unit in step S2 of FIG. 3. When the series of processes is started, the first derivation unit 116 derives the first hypercomplex number based on the detection result from the angular velocity sensor 108 in step S11. Next, in step S12, the second derivation unit 118 derives the second hypercomplex number based on the detection result from the angle sensor 110. Steps S11 and S12 may be executed in a reverse order. By the processes in step S11 and step S12, the first hypercomplex number and the second hypercomplex number are in a state of being able to be corrected in a complementary manner. Next, in step S13, the posture calculation unit 112 calculates the posture of the shank part 104 and generates posture information. The process in step S13 includes correcting the obtained posture information by the correction unit 122.

Next, the method of obtaining the posture of the shank part 104 by the posture calculation unit 112 will be described in detail. The posture of the shank part 104 refers to the orientation of the shank part 104 in a rotating coordinate system and the rotation that has caused the orientation. In order to obtain the posture of the shank part 104, the inclination angle is obtained by integrating a detected value from the angular velocity sensor 108. For convenience of explanation, a conventionally used calculation method will also be described in detail. Conventionally, Expressions 2 to 8 have been generally used to obtain the inclination angle.

First, rotating an arbitrary point r (x, y, z) of the shank part 104 in a coordinate system at rest by a quaternion q is expressed by the following Expression 2.

$$r' = qrq^* = (q_0 + q_1 i + q_2 j + q_3 k)(0 + xi + yj + zk)(q_0 - q_1 i - q_2 j - q_3 k) \quad \text{Expression 2}$$

where q* represents a conjugate quaternion.

Expression 2 represents that the point r has been rotated once based on the quaternion q. Applying this, when the point is continuously rotated by quaternions q1, q2, q3 ... qn, the quaternion q is expressed by the following Expression 3.

$$q = q_n \cdots q_3 q_2 q_1 \quad \text{Expression 3}$$

As shown in Expression 3, the posture calculation unit 112 feeds back a quaternion indicating the past rotation at the time of the next calculation.

Using Expression 3, a quaternion q(t) at time t becomes a quaternion q(t+Δt) after time Δt. When the rotation during this period is expressed by a quaternion q(Δt), the rotation is expressed by the following Expression 4.

$$q(t+\Delta t) = q(\Delta t) q(t) \quad \text{Expression 4}$$

In Expression 4, when it is assumed that the change in a vector n during the micro period of time Δt is due to a minute angle Δθ, the slope is expressed by the following Expression 5.

$$q(\Delta t) = \cos\frac{\Delta\theta}{2} + n\sin\frac{\Delta\theta}{2} \approx 1 + \frac{1}{2}n\Delta\theta \frac{q(t+\Delta t) - q(t)}{\Delta t} = \frac{1}{\Delta t}\left(\left(1 + \frac{1}{2}n\Delta\theta\right)q(t) - q(t)\right) = \frac{1}{2}\frac{\Delta\theta}{\Delta t}nq(t) \quad \text{Expression 5}$$

When the micro period of time Δt is brought as close to 0 as possible in Expression 5, the output obtained from the angular velocity sensor 108 represents a value obtained as a result of rotation by the quaternion q. Substituting this value into Expression 2 gives the following Expression 6.

$$\frac{\Delta\theta}{\Delta t}nq(l) = (q(l)\omega q(l)^*)q(l) = q(l)(\omega_1 i + \omega_2 j + \omega_3 k) \quad \text{Expression 6}$$

where ω represents the angular velocity measured by the angular velocity sensor.

Expression 7 is obtained by differentiating the quaternion q by time t for Expression 6.

$$\frac{dq}{dt} = \frac{1}{2}q(t)\omega = \frac{1}{2}(q_0 + q_1 i + q_2 j + q_3 k)(\omega_1 i + \omega_2 i + \omega_3 k) \quad \text{Expression 7}$$

Expression 8 can be obtained by rearranging Expression 7.

$$\frac{d}{dt}\begin{pmatrix} q_0 \\ q_1 \\ q_2 \\ q_3 \end{pmatrix} = \frac{1}{2}\begin{pmatrix} 0 & -\omega_1 & -\omega_2 & -\omega_3 \\ \omega_1 & 0 & \omega_3 & -\omega_2 \\ \omega_2 & -\omega_3 & 0 & \omega_1 \\ \omega_3 & \omega_2 & -\omega_1 & 0 \end{pmatrix}\begin{pmatrix} q_0 \\ q_1 \\ q_2 \\ q_3 \end{pmatrix} \quad \text{Expression 8}$$

Expression 8 is an expression used to integrate the detected value from the angular velocity sensor 108 so as to obtain the inclination angle.

Using Expression 8, the inclination angle of the shank part 104 can be obtained for the time being. However, when the inclination angle is iteratively calculated by Expression 8 in a state where the detected value from the angular velocity sensor 108 includes drift, an error due to the drift may be accumulated, and an accurate inclination angle may not be obtained. Further, in Expression 5, Δt is set to be as close to zero as possible. That is, Expression 8 is established only when the interval of the calculation by the posture calculation unit 112 is short.

Since it is difficult to completely eliminate errors that occur due to drift, it is sufficient if the result obtained by Expression 8 can be corrected based on the detection result from a sensor other than the angular velocity sensor 108, that is, the angle sensor 110. However, since the angle sensor 110 cannot accurately detect the rotation around the Z axis (yaw axis), it is difficult to correct the detection result from the angular velocity sensor 108 by directly using the detection result from the angle sensor 110.

In the knee joint 100 according to the embodiment, the rotation around the Z axis means turning performed in such a manner that the direction in which the wearer is facing is changed (for example, changing the direction while walking to the north so as to walk to the west). In other words, since the orientation of the wearer and the expansion and contraction motion of the drive auxiliary part 106 are not directly related to each other, the turning motion does not affect the control of the knee joint 100 (that is, the expansion and contraction motion of the drive auxiliary part 106). Paying attention to this point, the inventors have obtained a new finding that if the number of terms of a quaternion derived from a detection result from the angular velocity sensor 108 is reduced so that the rotation around the Z axis is ignored (considered as zero) so as to have the same number of terms as that in a detection result from the angle sensor 110, correction can be performed with a hypercomplex number in three dimensions derived from the detection result from the angle sensor 110. As a result, the detection result from the angular velocity sensor 108 can be corrected using the detection result from the angle sensor 110, or on the contrary, the detection result from the angle sensor 110 can be corrected using the detection result from the angular velocity sensor 108. Regarding this point, a further detailed explanation will be given in the following.

It is assumed that the current rotation of the shank part 104 obtained from the detection result from the angular velocity sensor 108 is expressed by a quaternion q'=(q0'+q1'i+q2'j+q3'k). This means that when the rotation around the Z axis is ignored, the shank part 104 may be rotated by an arbitrary angle θ according to the quaternion q'. Therefore, a value q" obtained by rotating the quaternion q' by the angle θ about the Z axis is expressed by the following Expression 9. The value q" indicates a hypercomplex number in three dimensions obtained by ignoring the rotation around the Z axis and reducing the number of terms by one with respect to the quaternion q'.

$$q'' = \left(\cos\frac{\theta}{2} + \sin\frac{\theta}{2}k\right)(q'_0 + q'_1 i + q'_2 j + q'_3 k)\left(q'_0\cos\frac{\theta}{2} - q'_3\sin\frac{\theta}{2}\right) + \\ \left(q'_1\cos\frac{\theta}{2} - q'_2\sin\frac{\theta}{2}\right)i + \\ \left(q'_2\cos\frac{\theta}{2} + q'_1\sin\frac{\theta}{2}\right)j + \left(q'_3\cos\frac{\theta}{2} + q'_0\sin\frac{\theta}{2}\right)k$$

Expression 9

Of the four terms of Expression 9, for example, if the term with k is to be set to 0, the following relationship as shown in Expression 10 is obtained.

$$\left(q'_3\cos\frac{\theta}{2} + q'_0\sin\frac{\theta}{2}\right) = \\ \sqrt{q'^2_0 + q'^2_3}\left(\sin\frac{\theta}{2}\frac{q'_0}{\sqrt{q'^2_0 + q'^2_3}} + \cos\frac{\theta}{2}\frac{q'_3}{\sqrt{q'^2_0 + q'^2_3}}\right) = \\ \sqrt{q'^2_0 + q'^2_3}\sin\left(\frac{\theta}{2} + \alpha\right)$$

Expression 10

According to Expression 10, the following is established:
  θ/2=−α

Based on Expression 10, the sine and cosine of the angle θ are expressed by the following Expression 11.

$$\cos\frac{\theta}{2} = \frac{q'_0}{\sqrt{q'^2_0 + q'^2_3}}, \sin\frac{\theta}{2} = -\frac{q'_3}{\sqrt{q'^2_0 + q'^2_3}}$$

Expression 11

Substituting Expression 11 into Expression 9 gives the following Expression 12.

$$q'' = \frac{q'^2_0 + q'^2_3}{\sqrt{q'^2_0 + q'^2_3}} + \frac{q'_0 q'_1 + q'_2 q'_3}{\sqrt{q'^2_0 + q'^2_3}}i + \\ \frac{q'_0 q'_2 - q'_1 q'_3}{\sqrt{q'^2_0 + q'^2_3}}j \\ = q''_0 + q''_1 i + q''_2 j$$

Expression 12

Expression 12 can also be expressed as the following Expression 13.

$$q'' = \cos\frac{\theta}{2} + \sin\frac{\theta}{2}\cos\alpha\, i + \sin\frac{\theta}{2}\sin\alpha\, j$$

Expression 13

In Expressions 12 and 13, the term with k is regarded as zero, and the rotation of the shank part 104 around the Z axis is ignored. However, considering the nature of the knee joint 100, this hypercomplex number in three dimensions can be also considered to be equivalent to the original quaternion. Expression 13 expresses that a new axis obtained by rotating the X axis by a predetermined angle around the Z axis is defined, and the shank part 104 is rotated around the new axis by the angle θ.

For example, the following calculation method is used when the first derivation unit 116 obtains the hypercomplex number q" in three dimensions after a time change based on the quaternion q derived from the current detection result from the angular velocity sensor 108. First, as shown in Expression 14, the current quaternion q is substituted into Expression 8 so as to calculate the quaternion q' after the time change.

$$q'_0 = q_0 + \frac{1}{2}(-\omega_1 q_1 - \omega_2 q_2)dt$$

$$q'_1 = q_1 + \frac{1}{2}(\omega_1 q_0 + \omega_3 q_2)dt$$

$$q'_2 = q_2 + \frac{1}{2}(\omega_2 q_0 - \omega_3 q_1)dt$$

$$q'_3 = 0 + \frac{1}{2}(\omega_3 q_0 + \omega_2 q_1 - \omega_1 q_2)dt$$

Expression 14

The equation q3=0 is established as described above.
Next, Expression 14 is substituted into the following Expression 15.

$$q''_0 = \frac{q'^2_0 + q'^2_3}{\sqrt{q'^2_0 + q'^2_3}} \\ = \frac{\left(q_0 + \frac{1}{2}(-\omega_1 q_1 - \omega_2 q_2)dt\right)^2 + \left(\frac{1}{2}(\omega_3 q_0 + \omega_2 q_1 - \omega_3 q_2)dt\right)^2}{\sqrt{\left(q_0 + \frac{1}{2}(-\omega_1 q_1 - \omega_2 q_2)dt\right)^2 + \left(\frac{1}{2}(\omega_3 q_0 + \omega_2 q_1 - \omega_3 q_2)dt\right)^2}}$$

Expression 15

This allows the hypercomplex number q" in three dimensions equivalent to the quaternion q' to be obtained. In Expression 15, since the value of a term with $dt^2$ is sufficiently small, when approximated to zero, Expression 15 can be expressed as the following Expression 16.

$$q_0'' = \sqrt{q_0^2 + q_0(-\omega_1 q_1 - \omega_2 q_2)dt}$$

$$= q_0\left(1 + \frac{1}{q_0}(-\omega_1 q_1 - \omega_2 q_2)dt\right)^{\frac{1}{2}}$$

$$= q_0\left(1 + \frac{1}{2q_0}(-\omega_1 q_1 - \omega_2 q_2)dt\right)$$

$$= q_0 + \frac{1}{2}(-\omega_1 q_1 - \omega_2 q_2)dt$$

Expression 16

When the same calculation is performed for hypercomplex numbers q1" and q2" in three dimensions, the following Expressions 17 and 18 are obtained.

$$q_1'' = q_1 + \frac{1}{2}\left(\omega_1 \frac{q_0^2 - q_2^2}{q_0} + \omega_2 \frac{q_1 q_2}{q_0} + 2\omega_3 q_2\right)dt$$

Expression 17

$$q_2'' = q_2 + \frac{1}{2}\left(\omega_1 \frac{q_1 q_2}{q_0} + \omega_2 \frac{q_0^2 - q_1^2}{q_0} - 2\omega_3 q_1\right)dt$$

Expression 18

By using Expressions 16 to 18, the inclination angle of the shank part 104 can be calculated as the hypercomplex number q" in three dimensions based on the previous hypercomplex number q in three dimensions and output ω obtained from the current detection result from the angular velocity sensor 108.

Next, an explanation will be given of a method by which the second derivation unit 118 calculates the posture of the shank part 104 from the detection result from the angle sensor 110. In this case, it is assumed that the angle sensor 110 is composed of a three-axis acceleration sensor. It is assumed that the output of the angle sensor 110 is a(ax, ay, az) and is normalized in advance such that the magnitude of the vector becomes one. Given that a hypercomplex number qa in three dimensions obtained from the detection result from the angle sensor 110 is qa=(qa0, qa1, qa2), acceleration measured in a rotating coordinate system in which gravitational acceleration (0, 0, −1) is rotated by the hypercomplex number qa in three dimensions is a. Therefore, the relationship in the following Expression 19 is established from an expression q*rq obtained when a point in a coordinate system at rest is viewed in a coordinate system rotated by the hypercomplex number qa in three dimensions.

$$\begin{pmatrix} a_x \\ a_y \\ a_z \end{pmatrix} = \begin{pmatrix} q_{a0}^2 + q_{a1}^2 - q_{a2}^2 & 2(q_{a1}q_{a2}) & 2(-q_{a0}q_{a2}) \\ 2(q_{a1}q_{a2}) & q_{a0}^2 - q_{a1}^2 + q_{a2}^2 & 2(q_{a0}q_{a1}) \\ 2(q_{a0}q_{a2}) & 2(-q_{a0}q_{a1}) & q_{a0}^2 - q_{a1}^2 - q_{a2}^2 \end{pmatrix} \begin{pmatrix} 0 \\ 0 \\ -1 \end{pmatrix}$$

Expression 19

The following Expressions 20 to 22 can be obtained by rearranging Expression 19.

$$a_x = 2q_{a0}q_{a2}$$ Expression 20

$$a_y = -2q_{a0}q_{a1}$$ Expression 21

$$a_z = -q_{a0}^2 + q_{a1}^2 + q_{a2}^2 = -2q_{a0}^2 + 1$$ Expression 22

From Expression 22, the relationship in Expression 23 can be obtained.

$$q_{a0} = \sqrt{\frac{1 - a_z}{2}}$$

Expression 23

Substituting Expression 23 into each of Expressions 20 and 21 gives the following Expressions 24 and 25.

$$q_{a1} = \frac{-a_y}{\sqrt{2 - 2a_z}}$$

Expression 24

$$q_{a2} = \frac{a_x}{\sqrt{2 - 2a_z}}$$

Expression 25

The hypercomplex number qa in three dimensions can be obtained from Expressions 23 through 25.

As described above, by calculating the posture of the shank part 104 while ignoring the rotation around the Z axis, the detection result from the angle sensor 110 and the detection result from the angular velocity sensor 108 can be treated as being in the same dimension. The posture calculation unit 112 treating the detection result from the angle sensor 110 and the detection result from the angular velocity sensor 108 as hypercomplex numbers in three dimensions allows for simplification of the calculation when, for example, the respective values are complementarily corrected with each other. That is, by treating the detection result from the angular velocity sensor 108 and the detection result from the angle sensor 110 as being in the same dimension, it is possible to create a state in which the detection result from the angular velocity sensor 108 can be corrected by using the detection result from the angle sensor 110. This provides an environment in which the detection value from the angular velocity sensor can be corrected according to various situations. For example, even if the detection result from the angular velocity sensor 108 includes an error due to drift, the error can be corrected by using the detection result from the angle sensor 110. The posture calculation unit 112 keeps calculating the posture repeatedly during driving. However, for example, when the wearer stops for a long time and there is a time interval from the previous posture calculation, an error can easily occur in the detection result from the angular velocity sensor 108. In addition, an energy saving mode that reduces the energy consumption of the entire knee joint 100 may be installed. It is assumed that the posture of the shank part 104 is calculated, for example, every 5 ms in a non-energy saving mode, whereas the posture of the shank part 104 is calculated, for example, every 100 ms in the energy saving mode. When the energy saving mode is started, the calculation frequency may become low, and the error in the detection result from the angular velocity sensor 108 may become large. In such a case, it is very useful to be able to correct the posture of the shank part 104 based on the detection result from the angle sensor 110.

Next, the correction by the correction unit 122 will be described in detail. The correction unit 122 repeatedly corrects the calculation result of the posture of the shank part 104 while the knee joint 100 is being driven. The correction unit 122 may make a correction every time the posture calculation unit 112 calculates the posture of the shank part 104 or may make a correction when predetermined conditions are satisfied. The predetermined conditions include when the mode is restored from the energy saving mode and when a predetermined time has elapsed since the previous correction is performed. Further, the predetermined conditions include when the control unit 114 controls the drive auxiliary part 106 based on a calculation result that has not been corrected for a predetermined number of times since the previous correction is performed. This is because there is a high possibility that the amount of drift included in the detection result from the angular velocity sensor 108 is large in such cases.

When the predetermined condition is set to perform the correction when a predetermined time has elapsed since the previous correction is performed, the correction unit 122 can use a first weighting coefficient A and a second weighting coefficient B that change according to the time elapsed since the previous correction is performed. The first and second weighting coefficients A and B are coefficients for determining how much the corresponding hypercomplex number is reflected in the correction result. When the hypercomplex number in three dimensions derived from the angular velocity sensor obtained by Expressions 16 to 18 is set as qg and the hypercomplex number in three dimensions derived from the angle sensor obtained by Expressions 23 to 25 is set as qa, the correction unit 122 can correct the calculation result of the posture of the shank part 104 by the following Expression 26.

$$qh = A \times qg + B \times qa \qquad \text{Expression 26}$$

where A+B=1 is established.

When the time elapsed since the previous correction is long, the value of the second weighting coefficient B can be increased such that the weight of the hypercomplex number in three dimensions that is based on the angle sensor 110 is increased, and the value of the first weighting coefficient A can be decreased such that the weight of the hypercomplex number in three dimensions that is based on the angular velocity sensor 108 is reduced. Thereby, a correction value qh that reduces the influence of the drift of the angular velocity sensor 108 can be obtained.

If the posture calculation unit 112 performs the correction every time the posture of the shank part 104 is calculated or if the posture calculation unit 112 is set to perform the correction when the control unit 114 controls the drive auxiliary part 106 based on a calculation result that has not been corrected for a predetermined number of times since the previous correction, the correction unit 122 can perform the correction by the following method.

In this case, the correction unit 122 may correct the posture of the shank part 104 using a complementary filter. From the detection result from the angle sensor 110, it is not possible to distinguish between vibration caused by a movement other than a walking movement and vibration caused by a change in the gravitational acceleration. Therefore, when vibration occurs, the detection result from the angle sensor 110 ends up including a large amount of noise. On the other hand, since the detection result from the angular velocity sensor 108 is not affected by vibration, it is considered that the noise is small in the short term. Therefore, for example, when the correction is performed at a short time interval, the correction is preferably performed such that while the detection result from the angular velocity sensor 108 is given weight, the influence of the drift of the angular velocity sensor 108 is cancelled with the detection result from the angle sensor 110. In this case, the correction unit 122 corrects the posture of the shank part 104 by the following Expression 27.

$$q_h = q_g + \alpha(q_a - q_g) \qquad \text{Expression 27}$$

where α is a predetermined constant.

By repeatedly using the complementary filter of Expression 27, the error of the angle sensor 110 is reduced by the constant α, and the error of the angular velocity sensor 108 is repeatedly corrected by α(qa−qg). As a result, the influence of drift can be reduced while suppressing the influence of vibration.

As another example, the correction unit 122 may correct the posture of the shank part 104 using a Kalman filter. The Kalman filter is represented by the following Expression 28.

$$q_h = q_g + K(q_a - q_g) \qquad \text{Expression 28}$$

$$K = \frac{\text{VARIANCE OF PREDICTED VALUE } (qg)}{\text{VARIANCE OF PREDICTED VALUE } + (qg) \text{ VARIANCE OF OBSERVED VALUE } (qa)}$$

The value K is a variable that is variable according to the variance of the detection result. For example, when the wearer is standing still, vibration due to terminal impact does not occur; therefore, it can be considered that unexpected vibration is unlikely to occur. In such a case, the variance of an observed value (qa) becomes small, and thus the value K becomes large. Therefore, the influence of the term K(qa−qg) on the correction value qh can be increased. On the contrary, when sudden vibration such as terminal impact occurs, the variance of the observed value (qa) becomes large, and the value of K becomes small. This allows the influence of the term K(qa−qg) on the correction value qh to be reduced. In this way, in the short term, more accurate correction can be performed by increasing or decreasing the correction amount according to the variance of the observed value from the angle sensor 110 on which noise can easily occur.

When the correction unit 122 corrects the posture of the shank part 104 using a Kalman filter, the correction unit 122 is also considered to have a function of correcting the calculation result from the posture calculation unit 112 according to the variance (that is, sudden vibration) of the observed value from the angle sensor 110. The correction unit 122 may change the variable K based on a change in amplitude and a change in frequency within a predetermined period.

As an alternative to the Kalman filter expressed by Expression 28, a filter expressed by the following Expression 29 may be used.

$$q_h = q_g + \frac{\mu}{|q_a - q_g|}(q_a - q_g) \qquad \text{Expression 29}$$

where μ is a constant.

In Expression 29, when the reliability of the angle sensor 110 is high, the value of a term (qa−qg) becomes small, and when the reliability of the angle sensor 110 is low, the value of the term (qa−qg) becomes large.

Expression 29 can also be expressed as the following Expressions 30 to 32.

$$q_{h1} = q_{g1} + \mu \frac{q_{a1} - q_{g1}}{\sqrt{(q_{a1} - q_{g1})^2 + (q_{a2} - q_{g2})^2 + (q_{a3} - q_{g3})^2}} \qquad \text{Expression 30}$$

$$q_{h2} = q_{g2} + \mu \frac{q_{a2} - q_{g2}}{\sqrt{(q_{a1} - q_{g1})^2 + (q_{a2} - q_{g2})^2 + (q_{a3} - q_{g3})^2}} \qquad \text{Expression 31}$$

$$q_{h3} = q_{g3} + \mu \frac{q_{a3} - q_{g3}}{\sqrt{(q_{a1} - q_{g1})^2 + (q_{a2} - q_{g2})^2 + (q_{a3} - q_{g3})^2}} \qquad \text{Expression 32}$$

Figure 5:
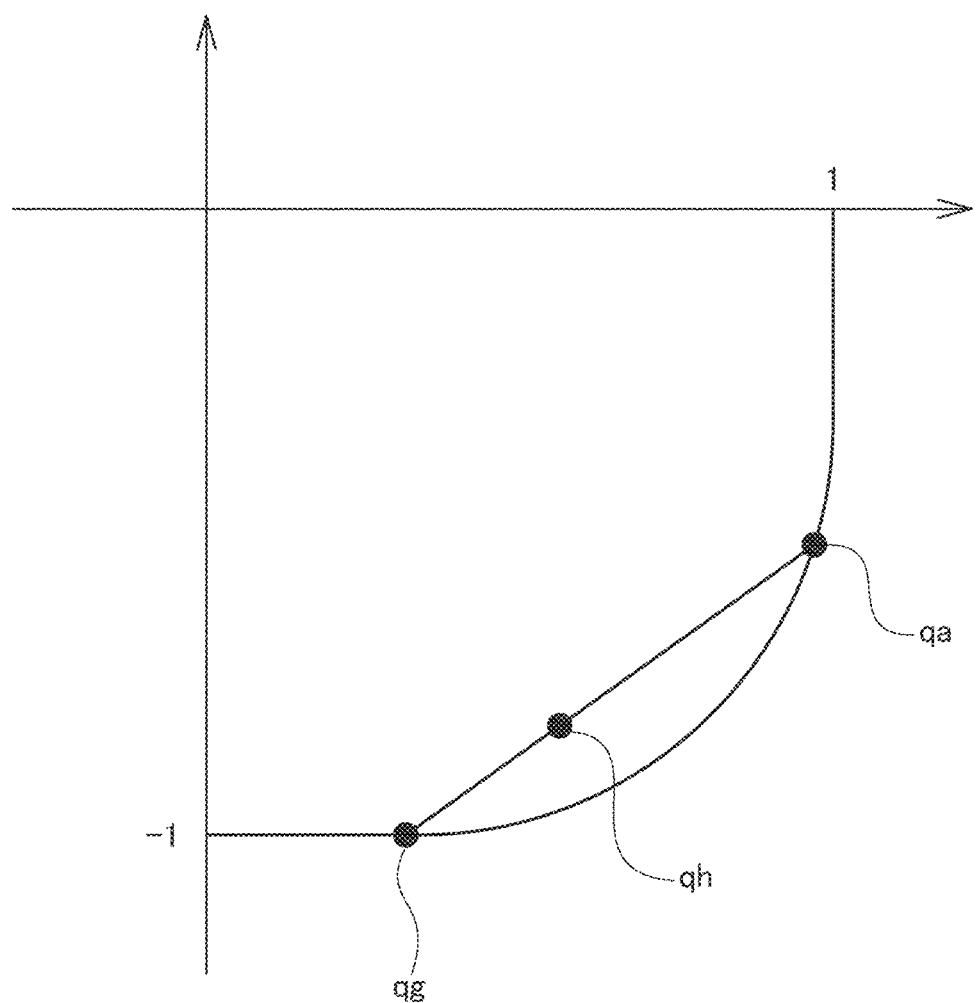
FIG. 5 is a graph showing the relationship between a value qa and a value qg.

FIG. 5 is a graph showing the relationship between a value qa and a value qg. More specifically, in FIG. 5, the value qa and the value qg are arranged in a normed space and are expressed on the assumption that the sizes of the respective vectors are the same. As shown in FIG. 5, the correction value qh is a value obtained by moving the correction value qh from the value qg toward the value qa by a fixed value μ. As can be understood from FIG. 5, the correction value qh always enters the inside of the arc in the normed space and becomes smaller than a value 1. However, the output a(ax, ay, az) from the angle sensor 110 is normalized in advance and fixed at a value 1, which is close to the value qa in Expression 29. Therefore, even if the correction unit 122 does not perform a calculation for normalizing the correction value qh at this stage, the correction value qh is stable at a value close to the value 1 (a value slightly smaller than the value 1). This allows the amount of calculation of the correction unit 122 to be reduced.

The posture information obtained by the posture calculation unit 112 or corrected posture information is supplied to the control unit 114 based on the determination by the posture calculation unit 112. For example, if a predetermined condition is set for correction, the posture calculation unit 112 supplies uncorrected posture information to the control unit 114 when the predetermined condition is not satisfied. The posture calculation unit 112 corrects the posture information only when the predetermined condition is satisfied and supplies the corrected posture information to the control unit 114. The posture calculation unit 112 may calculate posture information and corrected posture information in all cases so as to supply the posture information and the corrected posture information to the control unit 114, and the control unit 114 may determine a predetermined condition so as to determine posture information to be used.

Next, a method of calibrating the angular velocity sensor 108 by the calibration unit 124 will be described. The calibration unit 124 estimates the drift of the angular velocity sensor 108 using the hypercomplex number in three dimensions obtained by the first derivation unit 116 and brings the bias close to zero. For example, if a detection result from the angular velocity sensor 108 is obtained even when the wearer is not moving, it can be considered that drift has occurred. In this case, the calibration unit 124 handles the average value of detection results from the angular velocity sensor 108 as the detection result from the angular velocity sensor 108. Further, the calibration unit 124 may calibrate the detection result from the angular velocity sensor 108 by applying the filter according to Expression 29 to values obtained by Expressions 16 to 18. The calibration unit 124 may perform calibration every time a detection result from the angular velocity sensor 108 is obtained or may perform calibration when the above-mentioned predetermined conditions are satisfied.

By providing the calibration unit 124, the accuracy of the detection result from the angular velocity sensor 108 can be improved. Especially in a specific device such as the above-knee prosthesis 10, it is difficult for the user to perform calibration while holding the device in the right position. Therefore, by allowing the calibration unit 124 to continuously calibrate the angular velocity sensor 108, an effect can be also obtained where the burden on the user can be reduced.

Next, a process of the control unit in step S3 will be described. As described above, the posture information is supplied as a hypercomplex number in three dimensions. The control unit 114 controls the posture of the shank part 104 based on the posture information including the supplied hypercomplex number in three dimensions. The control unit 114 controls the amount of expansion and contraction of the drive auxiliary part 106 based on a pitch angle p and a roll angle r obtained in the following example.

A quaternion expressing a rotation by the pitch angle p followed by a rotation by the roll angle r is expressed by the following Expression 33 using Expressions 1 and 3.

$$\begin{aligned} q &= \left(\cos\frac{r}{2} + \sin\frac{r}{2}i\right)\left(\cos\frac{p}{2} + \sin\frac{p}{2}j\right) \\ &= \cos\frac{r}{2}\cos\frac{p}{2} + \sin\frac{r}{2}\cos\frac{p}{2}i + \cos\frac{r}{2}\sin\frac{p}{2}j + \sin\frac{r}{2}\sin\frac{p}{2}k \end{aligned} \qquad \text{Expression 33}$$

When Expression 33 is converted into a hypercomplex number in three dimensions using Expression 12, the following Expressions 34 to 36 are obtained.

$$\begin{aligned} q_0 &= \sqrt{\cos^2\frac{r}{2}\cos^2\frac{p}{2} + \sin^2\frac{r}{2}\sin^2\frac{p}{2}} \\ &= \sqrt{\frac{1+\cos r}{2}\frac{1+\cos p}{2} + \frac{1-\cos r}{2}\frac{1-\cos p}{2}} \\ &= \sqrt{\frac{1+\cos p \cos r}{2}} \end{aligned} \qquad \text{Expression 34}$$

$$q_1 = \frac{\cos\frac{r}{2}\cos\frac{p}{2}\sin\frac{r}{2}\cos\frac{p}{2} - \cos\frac{r}{2}\sin\frac{p}{2}\sin\frac{r}{2}\sin\frac{p}{2}}{\sqrt{\cos^2\frac{r}{2}\cos^2\frac{p}{2} + \sin^2\frac{r}{2}\sin^2\frac{p}{2}}} =$$
$$\frac{1}{q_0}\left(\cos\frac{r}{2}\sin\frac{r}{2}\left(\cos^2\frac{p}{2} - \sin^2\frac{p}{2}\right)\right)$$
$$= \frac{1}{2q_0}\sin r\cos p$$

Expression 35

$$q_2 = \frac{\cos\frac{r}{2}\cos\frac{p}{2}\cos\frac{r}{2}\sin\frac{p}{2} + \sin\frac{r}{2}\cos\frac{p}{2}\sin\frac{r}{2}\sin\frac{p}{2}}{\sqrt{\cos^2\frac{r}{2}\cos^2\frac{p}{2} + \sin^2\frac{r}{2}\sin^2\frac{p}{2}}} =$$
$$\frac{1}{q_0}\left(\cos\frac{p}{2}\sin\frac{p}{2}\left(\cos^2\frac{r}{2} + \sin^2\frac{r}{2}\right)\right)$$
$$= \frac{1}{2q_0}\sin p$$

Expression 36

The following Expression 37 can be obtained by rearranging Expression 36 for p.

$$p = a\sin(2q_0 q_2)$$

Expression 37

When Expressions 34 and 35 are rearranged, the following Expression 38 can be obtained.

$$\cos r = \frac{2q_0^2 - 1}{\cos p}, \sin r = \frac{2q_0 q_1}{\cos p}.$$

Expression 38

From Expression 38, r=a tan 2(2q0q1, 2q0²−1) is obtained.

The control unit 114 controls the drive auxiliary part 106 based on results obtained by Expressions 37 and 38.

Further, when a term including a value q0 exists in the denominator as in Expression 17, the posture calculation unit 112 may perform the following process.

For example, in Expression 17, the calculation is performed ignoring a squared term with dt on the assumption that the value q0 is sufficiently large. However, when the value q0 is small (that is, when the knee joint 100 is rotated by nearly 180 degrees in a fixed coordinate system), there is a possibility that the term containing the value q0 in the denominator cannot be ignored. Therefore, when the knee joint 100 is rotated by nearly 180 degrees in a coordinate system at rest, the posture calculation unit 112 rotates the coordinate system as follows so as to calculate the posture.

Figure 6:
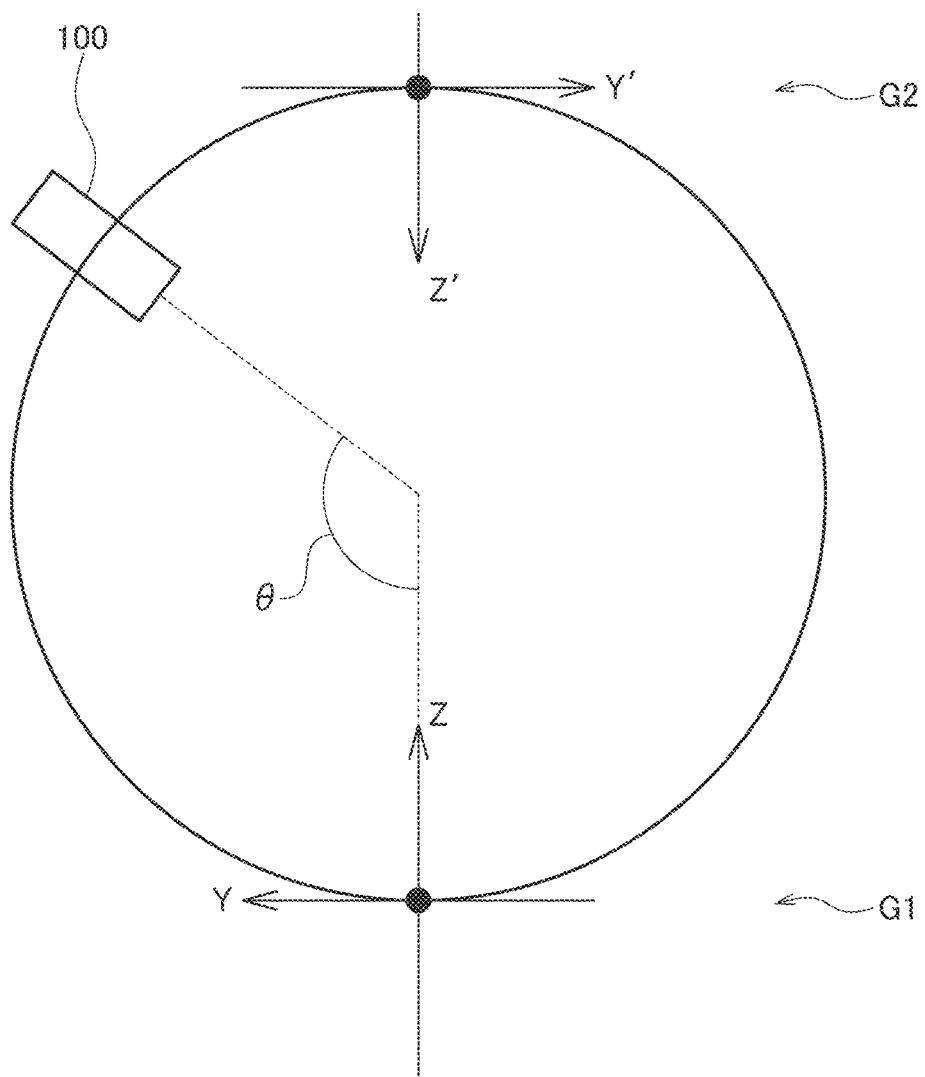
FIG. 6 shows a schematic view of the knee joint.

FIG. 6 shows a schematic view of the knee joint. As shown in FIG. 6, the posture calculation unit 112 calculates the posture using a coordinate system G1 at rest (first coordinate system) in the lower hemisphere when the value q0 is large and calculates the posture using a coordinate system G2 at rest (second coordinate system) obtained by converting the coordinate system G1 at rest in the upper hemisphere when the value q0 is small. When the posture is calculated using the coordinate system G1 at rest and the coordinate system G2 at rest, the calculation for the rotation angle may be performed while keeping the orientation of the rotation axis and adding 180 degrees to the rotation angle in the coordinate system G1 at rest.

For the conversion of a coordinate system, the following Expressions 39 to 44 are used.

$$q = \cos\frac{\theta}{2} + \sin\frac{\theta}{2}\cos\alpha\, i + \sin\frac{\theta}{2}\sin\alpha\, j$$

Expression 39

$$q_0 = \cos\frac{\theta}{2}, q_1 = \sin\frac{\theta}{2}\cos\alpha, q_2 = \sin\frac{\theta}{2}\sin\alpha$$

Expression 40

$$q' = \cos\frac{\theta+\pi}{2} + \sin\frac{\theta+\pi}{2}\cos\alpha\, i + \sin\frac{\theta+\pi}{2}\sin\alpha\, j$$

Expression 41

$$q'_0 = \cos\frac{\theta+\pi}{2} = -\sin\frac{\theta}{2}$$

Expression 42

$$q'_1 = \sin\frac{\theta+\pi}{2}\cos\alpha = \cos\frac{\theta}{2}\cos\alpha$$

Expression 43

$$q'_2 = \sin\frac{\theta+\pi}{2}\sin\alpha = \cos\frac{\theta}{2}\sin\alpha$$

Expression 44 where θ indicates the rotation angle of the original hypercomplex number q in three dimensions before the conversion, and α indicates the angle formed by the rotation axis and the X axis. Further, a hypercomplex number q' in three dimensions after the conversion is shown on the assumption that the rotation axis is the same and a rotation angle π has been added. Further, in Expressions 42 to 44, since q0' is a positive value, it is necessary to invert all the signs in the expression when the angle θ is a positive value.

When Expressions 40 and 42 are rearranged, the following Expression 45 can be obtained.

$$q'_0 = \sqrt{1 - \cos^2\frac{\theta}{2}} = \sqrt{1 - q_0^2}$$

Expression 45

When Expressions 40 and 43 are rearranged, the following Expression 46 can be obtained.

$$q'_1 = \cos\frac{\theta}{2}\cos\alpha = q_0\frac{q_1}{\sin\frac{\theta}{2}} = -\frac{q_0 q_1}{\sqrt{1 - q_0^2}}$$

Expression 46

When Expressions 40 and 44 are rearranged, the following Expression 47 can be obtained.

$$q'_2 = \cos\frac{\theta}{2}\sin\alpha = q_0\frac{q_2}{\sin\frac{\theta}{2}} = -\frac{q_0 q_2}{\sqrt{1 - q_0^2}}$$

Expression 47

By such coordinate conversion, a highly accurate correction value can be obtained even when the value q0 is small.

Figure 7:
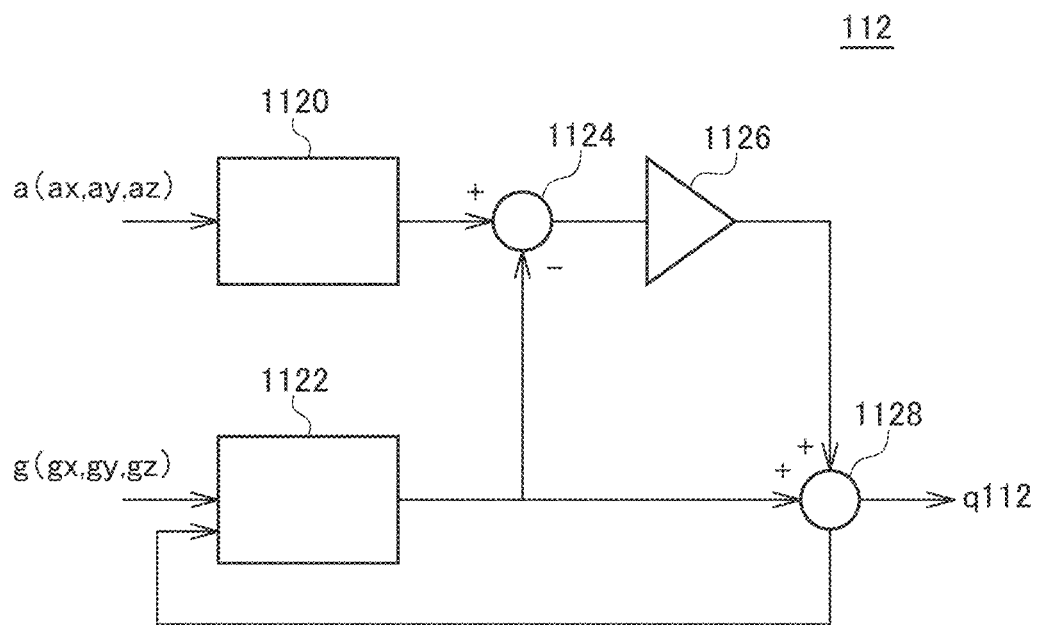
FIG. 7 is a block diagram showing a series of processes performed by a posture calculation unit.

FIG. 7 is a block diagram showing a series of processes performed by the posture calculation unit. FIG. 7 illustrates a mode in which the correction is performed every time the posture information is calculated in order to simplify the illustration. As shown in FIG. 7, the posture calculation unit 112 derives a hypercomplex number in three dimensions from a detection result from the angle sensor 110 in a component 1120. This process is executed by the second derivation unit 118 using Expressions 23 to 25. The posture calculation unit 112 derives a hypercomplex number in three dimensions from a detection result from the angular velocity sensor 108 in a component 1122. This process is executed by the first derivation unit 116 using Expressions 16 to 18. In a component 1124, the posture calculation unit 112 derives the difference between the output of the component 1120 and the output of the component 1122. This difference is filtered in a component 1126 (e.g., Expression 29) and then output to a component 128 as a correction value. In a component 1128, the sum of the hypercomplex number in three dimensions obtained in the component 1122 and the correction value obtained in the component 1126 is derived. In other words, in the component 1122, the posture information of the shank part 104 once calculated in the component 1122 is corrected by the correction value. The corrected posture information is supplied to the control unit 114 as output q112 from the posture calculation unit 112. Further, the output q112 from the component 1128 is fed back to the component 1122 and used for the next calculation. In this case, the correction result is substituted into qg1 in Expression 30.

Figure 8:
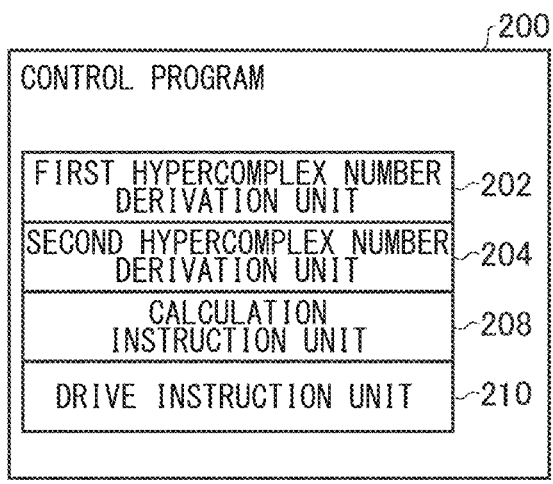
FIG. 8 is a block diagram of a control program for controlling a knee joint.

FIG. 8 is a block diagram of a control program for controlling the knee joint. The program is stored in a computer-readable medium. As shown in FIG. 8, a control program 200 includes a first hypercomplex number derivation unit 202, a second hypercomplex number derivation unit 204, a calculation instruction unit 208, and a drive instruction unit 210.

The first hypercomplex number derivation unit 202 supplies an instruction to derive a hypercomplex number in three dimensions to the first derivation unit 116 based on the detection result from the angular velocity sensor 108. The second hypercomplex number derivation unit 204 supplies an instruction to derive a hypercomplex number in three dimensions to the second derivation unit 118 based on the detection result from the angle sensor 110. The calculation instruction unit 208 supplies an instruction to calculate the posture of the knee joint 100 to the posture calculation unit 112 based on the two hypercomplex numbers in three dimensions that have been obtained. The instruction from the calculation instruction unit 208 includes an instruction to cause the correction unit 122 to correct the posture information according to a predetermined condition. The drive instruction unit 210 supplies an instruction to control the drive auxiliary part 106 to the control unit 114 based on the calculation result from the calculation instruction unit 208.

As described above, according to the knee joint 100, an environment can be prepared in which one of the two detection results obtained from the angular velocity sensor 108 and the angle sensor 110 can be used to correct the other. Once the environment that allows for the correction is prepared, the detection results from both can be corrected in a complementary manner using a simple filter.

Further, by using the first weighting coefficient A and the second weighting coefficient B, correction can be performed that weights the detection result from the angle sensor 110 when there is a high possibility that the reliability of the detection result from the angular velocity sensor 108 is lowered. Thereby, the accuracy of posture calculation can be improved.

Further, when the predetermined condition is not satisfied, the control unit 114 controls the drive auxiliary part 106 based only on the detection result from the angular velocity sensor 108, and the time required for the calculation can be thereby shortened, improving the response speed of the knee joint 100.

The present invention is not limited to the above-described embodiment, and each feature of the embodiment can be appropriately changed without departing from the scope of the present invention.

In particular, the present invention is not limited to the knee joint and can be applied to a device that does not affect the calculation of posture even when rotation around the Z axis is ignored. The present invention can be applied to a device that does not need to take the traveling direction into consideration when controlling the posture or a rotating body that does not affect the calculation of posture even when rotation in the pitch direction is ignored. When the present invention is implemented as a posture calculator that calculates the posture of a moving object, a hypercomplex number in three dimensions derived from the angular velocity of the moving object and a hypercomplex number in three dimensions derived from the detection result of the angle of the moving object in a coordinate system at rest need to be used.

APPENDIX

The invention according to each of the above-described embodiments may be specified by the items described below.

Item 1. A knee joint comprising:
 a thigh connection part to which a socket that fits over the user's thigh is connected;
 a shank part that is connected to the thigh connection part and provided rotatably around a predetermined axis;
 a drive auxiliary part that connects the thigh connection part and the shank part and limits or assists rotational movement of the shank part around the predetermined axis with respect to the thigh connection part;
 an angular velocity sensor that detects an angular velocity of the shank part;
 an angle sensor that detects an angle of the shank part with respect to a coordinate system at rest;
 a posture calculation unit that calculates the posture of the shank part based on a first hypercomplex number that is derived based on a detection result from the angular velocity sensor and a second hypercomplex number that is derived based on a detection result from the angle sensor and that has the same number of terms as that of the first hypercomplex number; and
 a control unit that controls the drive auxiliary part based on a calculation result from the posture calculation unit.

Item 2. The knee joint according to item 1, wherein the posture calculation unit includes a correction unit that corrects the calculation result of the posture of the shank part by using the first hypercomplex number and the second hypercomplex number.

Item 3. The knee joint according to item 2, wherein the correction unit corrects the calculation result of the posture of the shank part by using a complementary filter including a first weighting coefficient relating to the detection result from the angular velocity sensor and a second weighting coefficient relating to the detection result from the angle sensor where the first weighting coefficient and the second weighting coefficient can be changed.

Item 4. The knee joint according to item 3, wherein
 the correction unit repeatedly performs correction, and
 the first weighting coefficient and the second weighting coefficient are changed according to time elapsed since the last correction performed by the correction unit.

Item 5. The knee joint according to any one of items 1 to 4, wherein
 the posture calculation unit includes:
 a first derivation unit that derives a quaternion based on the detection result from the angular velocity sensor and converts the quaternion into a hypercomplex number in three dimensions while treating an arbitrary term of the quaternion as zero; and a second derivation unit that derives a hypercomplex number in three dimensions as the second hypercomplex number based on the detection result from the angle sensor.

Item 6. The knee joint according to any one of items 2 to 5, wherein every time the control unit controls the drive auxiliary part based only on the first hypercomplex number for a predetermined number of times, the control unit controls the drive auxiliary part based on the calculation result corrected by the correction unit.

Item 7. The knee joint according to item 5, wherein when the last control of the drive auxiliary part is based on the corrected calculation result, the first derivation unit derives the hypercomplex number in three dimensions using the calculation result used in the last control of drive auxiliary part.

Item 8. The knee joint according to any one of items 1 to 7, wherein the posture calculation unit calculates the posture while treating the rotation value around the vertical direction in the coordinate system at rest as zero.

Item 9. The knee joint according to any one of items 1 to 8, wherein the posture calculation unit calculates the posture using a first coordinate system when the angle of the shank part with respect to the thigh connection part is less than a predetermined angle and calculates the posture using a second coordinate system obtained by rotating the first coordinate system when the angle of the shank part with respect to the socket is equal to or greater than the predetermined angle.

Item 10. The knee joint according to any of items 1 to 9, comprising a calibration unit that calibrates the angular velocity sensor using the detection result from the angle sensor.

Item 11. A posture calculator that calculates the posture of a moving object based on the number of terms in a first hypercomplex number derived based on a detection result from an angular velocity sensor for detecting an angular velocity of the moving object and the number of terms in a second hypercomplex number that is derived based on a detection result from an angle sensor for detecting an angle of the moving object and that has the same number of terms as that of the first hypercomplex number.

Item 12. The posture calculator according to item 11, comprising:
 a first derivation unit that derives a hypercomplex number in three dimensions as the first hypercomplex number based on the detection result from the angular velocity sensor;
 a second derivation unit that derives a hypercomplex number in three dimensions as the second hypercomplex number based on the detection result from the angle sensor; and
 a correction unit that corrects a calculation result of the posture of the moving object by using the hypercomplex number in three dimensions derived by the first derivation unit and the hypercomplex number in three dimensions derived by the second derivation unit.

Item 13. The posture calculator according to item 11 or 12, comprising a calibration unit that calibrates the angular velocity sensor using the detection result from the angle sensor.

Item 14. A method of controlling a knee joint, wherein the knee joint includes:
 a thigh connection part to which a socket that fits over the user's thigh is connected;
 a shank part that is connected to the thigh connection part and provided rotatably around a predetermined axis;
 a drive auxiliary part that connects the thigh connection part and the shank part and limits or assists rotational movement of the shank part around the predetermined axis with respect to the thigh connection part;
 an angular velocity sensor that detects an angular velocity of the shank part;
 an angle sensor that detects an angle of the shank part with respect to a coordinate system at rest;
 a posture calculation unit that calculates a posture of the shank part based on a first hypercomplex number that is derived based on a detection result from the angular velocity sensor and a second hypercomplex number that is derived based on a detection result from the angle sensor and that has the same number of terms as that of the first hypercomplex number; and
 a control unit that controls the drive auxiliary part based on a calculation result from the posture calculation unit,
 the method comprising:
 deriving a first hypercomplex number based on a detection result from the angular velocity sensor and deriving a second hypercomplex number that has the same number of terms as that of the first hypercomplex number based on a detection result from the angle sensor;
 calculating the posture of the knee joint based on the first hypercomplex number and the second hypercomplex number; and
 controlling the drive auxiliary part based on the calculated posture of the knee joint.

Item 15. A non-transitory computer-readable medium recording a program for controlling a knee joint, wherein the knee joint includes:
 a thigh connection part to which a socket that fits over the user's thigh is connected;
 a shank part that is connected to the thigh connection part and provided rotatably around a predetermined axis;
 a drive auxiliary part that connects the thigh connection part and the shank part and limits or assists rotational movement of the shank part around the predetermined axis with respect to the thigh connection part;
 an angular velocity sensor that detects an angular velocity of the shank part;
 an angle sensor that detects an angle of the shank part with respect to a coordinate system at rest;
 a posture calculation unit that calculates a posture of the shank part based on a first hypercomplex number that is derived based on a detection result from the angular velocity sensor and a second hypercomplex number that is derived based on a detection result from the angle sensor and that has the same number of terms as that of the first hypercomplex number; and
 a control unit that controls the drive auxiliary part based on a calculation result from the posture calculation unit,
 the program comprising:
 a first derivation module that causes the posture calculation unit to derive a first hypercomplex number based on the detection result from the angular velocity sensor;
 a second derivation module that causes the posture calculation unit to derive a second hypercomplex number having a different number of terms from that of the first hypercomplex number based on the detection result from the angle sensor;
 a calculation instruction module that causes the posture calculation unit to calculate the posture of the knee joint based on the first hypercomplex number and the second hypercomplex number; and a drive instruction module that causes the control unit to control the drive auxiliary part based on a calculation result from the calculation instruction module.

Item 16. A non-transitory computer-readable medium recording a program for controlling a posture calculator, wherein the posture calculator calculates a posture of a moving object based on a first hypercomplex number derived based on a detection result from an angular velocity sensor for detecting an angular velocity of the moving object and a second hypercomplex number that is derived based on a detection result from an angle sensor for detecting an angle of the moving object and that has the same number of terms as that of the first hypercomplex number, the program comprising:
- a first derivation module that causes the posture calculator to derive a first hypercomplex number based on the detection result from the angular velocity sensor;
- a second derivation module that causes the posture calculator to derive a second hypercomplex number having a different number of terms from that of the first hypercomplex number based on the detection result from the angle sensor; and
- a calculation instruction module that causes the posture calculator to calculate the posture of the knee joint based on the first hypercomplex number and the second hypercomplex number.

What is claimed is:

1. A knee joint comprising:
- a thigh connection part to which a socket that fits over a thigh of a user is connected;
- a shank part that is a moving object connected to the thigh connection part and provided rotatably around a predetermined axis;
- a drive auxiliary part that connects the thigh connection part and the shank part and limits or assists rotational movement of the shank part around the predetermined axis with respect to the thigh connection part;
- an angular velocity sensor that detects an angular velocity of the shank part;
- an angle sensor that detects an angle of the shank part with respect to a coordinate system at rest;
- a posture calculator that calculates a posture of the moving object based on a first hypercomplex number derived based on a detection result from the angular velocity sensor for detecting an angular velocity of the moving object and a second hypercomplex number that is derived based on a detection result from the angle sensor for detecting an angle of the moving object and that has the same number of terms as that of the first hypercomplex number; and
- a control unit that controls the drive auxiliary part based on a calculation result from the posture calculator, wherein
- the posture calculator calculates a posture of the shank part based on the first hypercomplex number that is derived based on the detection result from the angular velocity sensor and the second hypercomplex number that is derived based on the detection result from the angle sensor and that has the same number of terms as that of the first hypercomplex number.

2. The knee joint according to claim 1, wherein the posture calculator includes a correction unit that corrects the calculation result of the posture of the shank part by using the first hypercomplex number and the second hypercomplex number.

3. The knee joint according to claim 2, wherein the correction unit corrects the calculation result of the posture of the shank part by using a complementary filter including a first weighting coefficient relating to the detection result from the angular velocity sensor and a second weighting coefficient relating to the detection result from the angle sensor where the first weighting coefficient and the second weighting coefficient can be changed.

4. The knee joint according to claim 3, wherein
the correction unit repeatedly performs correction, and
the first weighting coefficient and the second weighting coefficient are changed according to time elapsed since the last correction performed by the correction unit.

5. The knee joint according to claim 2, wherein every time the control unit controls the drive auxiliary part based only on the first hypercomplex number for a predetermined number of times, the control unit controls the drive auxiliary part based on the calculation result corrected by the correction unit.

6. The knee joint according to claim 1, wherein
the posture calculator includes:
- a first derivation unit that derives a quaternion based on the detection result from the angular velocity sensor and converts the quaternion into a hypercomplex number in three dimensions while treating an arbitrary term of the quaternion as zero; and
- a second derivation unit that derives a hypercomplex number in three dimensions as the second hypercomplex number based on the detection result from the angle sensor.

7. The knee joint according to claim 6, wherein when the last control of the drive auxiliary part is based on the corrected calculation result, the first derivation unit derives the hypercomplex number in three dimensions using the calculation result used in the last control of drive auxiliary part.

8. The knee joint according to claim 1, wherein the posture calculator calculates the posture while treating the rotation value around the vertical direction in the coordinate system at rest as zero.

9. The knee joint according to claim 1, wherein the posture calculator calculates the posture using a first coordinate system when the angle of the shank part with respect to the thigh connection part is less than a predetermined angle and calculates the posture using a second coordinate system obtained by rotating the first coordinate system when the angle of the shank part with respect to the socket is equal to or greater than the predetermined angle.

10. The knee joint according to claim 1, comprising a calibration unit that calibrates the angular velocity sensor using the detection result from the angle sensor.

11. A method of controlling a knee joint which includes:
- a thigh connection part to which a socket that fits over a thigh of a user is connected;
- a shank part that is connected to the thigh connection part and provided rotatably around a predetermined axis;
- a drive auxiliary part that connects the thigh connection part and the shank part and limits or assists rotational movement of the shank part around the predetermined axis with respect to the thigh connection part;
- an angular velocity sensor that detects an angular velocity of the shank part;
- an angle sensor that detects an angle of the shank part with respect to a coordinate system at rest;
- a posture calculation unit that calculates a posture of the shank part based on a first hypercomplex number that is derived based on a detection result from the angular velocity sensor and a second hypercomplex number that is derived based on a detection result from the angle sensor and that has the same number of terms as that of the first hypercomplex number; and a control unit that controls the drive auxiliary part based on a calculation result from the posture calculation unit, the method comprising:

deriving a first hypercomplex number based on a detection result from the angular velocity sensor and deriving a second hypercomplex number that has the same number of terms as that of the first hypercomplex number based on a detection result from the angle sensor;

calculating the posture of the knee joint based on the first hypercomplex number and the second hypercomplex number; and controlling the drive auxiliary part based on the calculated posture of the knee joint.

12. A non-transitory computer-readable medium recording a program for controlling a posture calculator, wherein the posture calculator calculates a posture of a moving object based on a first hypercomplex number derived based on a detection result from an angular velocity sensor for detecting an angular velocity of the moving object and a second hypercomplex number that is derived based on a detection result from an angle sensor for detecting an angle of the moving object and that has the same number of terms as that of the first hypercomplex number, the program comprising:

a first derivation module that causes the posture calculator to derive a first hypercomplex number based on the detection result from the angular velocity sensor;

a second derivation module that causes the posture calculator to derive a second hypercomplex number having a different number of terms from that of the first hypercomplex number based on the detection result from the angle sensor; and a calculation instruction module that causes the posture calculator to calculate the posture of the knee joint based on a first hypercomplex number and the second hypercomplex number.

* * * * *